United States Patent [19]

Fitzgerald et al.

[11] Patent Number: 4,754,640
[45] Date of Patent: Jul. 5, 1988

[54] APPARATUS AND METHOD FOR DETERMINING THE VISCOELASTICITY OF LIQUIDS

[75] Inventors: J. Vincent Fitzgerald, Metuchen; Frank J. Matusik, Piscataway; Donald W. Nelson, Voorhees, all of N.J.; John L. Schrag, Madison, Wis.

[73] Assignee: National Metal and Refining Company, Ltd., Metuchen, N.J.

[21] Appl. No.: 26,869

[22] Filed: Mar. 17, 1987

[51] Int. Cl.$^4$ .................................................. G01N 11/16
[52] U.S. Cl. .................................................. 73/54; 73/59
[58] Field of Search .................. 73/54, 59, 60, 1 DV; 137/92

[56] References Cited

U.S. PATENT DOCUMENTS

| | | | |
|---|---|---|---|
| 3,710,614 | 1/1973 | Oppliger | 73/54 |
| 3,712,117 | 1/1973 | Fitzgerald et al. | 73/59 |
| 3,762,429 | 10/1973 | Fitzgerald et al. | 137/92 |
| 3,796,088 | 3/1974 | Gustafsson et al. | 73/59 |
| 4,166,381 | 9/1979 | Woo | 73/54 |
| 4,488,427 | 12/1984 | Matusik et al. | 73/59 |
| 4,524,610 | 6/1985 | Fitzgerald et al. | 73/54 |
| 4,558,588 | 12/1985 | Beaudoin et al. | 73/54 |

FOREIGN PATENT DOCUMENTS

| | | | |
|---|---|---|---|
| 15838 | 1/1984 | Japan | 73/54 |
| 166840 | 9/1984 | Japan | 73/54 |
| 830463 | 3/1960 | United Kingdom | 73/59 |

Primary Examiner—Stewart J. Levy
Assistant Examiner—Hezron E. Williams
Attorney, Agent, or Firm—Arthur L. Lessler

[57] ABSTRACT

A rheometer for determining the viscoelasticity of a liquid from the mechanical impedance which the liquid presents to an oscillating surface. The incremental power required to maintain a fixed amplitude of oscillation of the surface upon immersion in the liquid is determined. The differential shift in oscillation frequency due to immersion in the liquid is also determined. By relating (i) the incremental oscillation power to mechanical resistance presented by the liquid to the oscillating surface, and (ii) the differential shift in a oscillation frequency to the mechanical reactance presented by the liquid to the oscillating surface, the viscoelasticity of the liquid is determined. Applications include laboratory measurements and process control.

10 Claims, 6 Drawing Sheets

APPARATUS AND METHOD FOR DETERMINING THE VISCOELASTICITY OF LIQUIDS

BACKGROUND OF THE INVENTION

This invention relates to a method and apparatus for the determination of the viscoelasticity of liquids. The apparatus constitutes a rheometer that measures the complex [i.e. the (i) resistive and (ii) reactive components of the] mechanical impedance presented by a liquid to an oscillating surface of a transducer. The Viscoelastic properties of sample liquids are determined from the measured mechanical impedance.

The transducer and associated circuitry of the rheometer are of the general type disclosed in U.S. Pat. Nos. 3,710,614; 3,712,117; 3,762,429; 3,875,791, 4,299,119; 4,488,427; and 4,524,610. Also see the article entitled "Oscillation Viscometer", published by J. V. Fitzgerald and F. J. Matusik in the June 1986 issue of Measurements and Control.

While all liquids impede the motion of an oscillating surface, there is a large class of liquids from whose impedance their viscoelasticity can be determined. Polymeric liquids belong to this class.

The viscoelasticities (and other rheological properties) of polymeric liquids are important to the plastics industry. As a result, in recent years there has been great effort to develop instrumentation for rheological laboratory and inprocess measurement.

Instrumentation for the determination of the viscoelasticity of polymeric fluids in tanks and pipes has been diligently sought by operating engineers. It is well known that better uniformity in product could be more efficiently achieved if the viscous and elastic responses of the polymeric liquid could be adjusted during processing.

In process control two types of rheometers can be used, namely online and inline types, the inline type being preferred. In an online device a sample of liquid is diverted from a main pipe or vessel for measurement. In an inline device the measurement is made directly inside the pipe or vessel while the liquid is flowing, stirred, or stationary—i.e. without interrupting the process and without removing the liquid from its processing path.

A number of instruments have been developed for providing laboratory (and in a few instances, online) viscoelasticity data, as discussed below. However, there is need for an inline rheometer which measures viscoelasticity.

Prior Viscoelasticity Rheometers

General principles involved in impedance measurements of viscoelasticity are discussed in "Relaxations in Polymers, Liquids, Gels" by W. Phillippoff, published in Physical Acoustics, Mason, II-B, Academic Press, N.Y. (1965).

Two types of viscoelasticity determining rheometers are sold by Haake Buchler Instruments, Inc., 244 Saddle River Road, P.O. Box 549, Saddle Brook, N.J. 07662. One of these employs a relaxation method, while the other employs a dynamic method.

In the relaxation type of viscoelasticity rheometer sold by Haake, the liquid is sheared for a defined period of time in a Haake Rotovisco viscometer. When the shearing is suddenly stopped, the decay of the force (as a function of time) is recorded. The complex modulus is determined from the decay curve.

The dynamic type of viscoelasticity rheometer sold by Haake employs a Haake RV/CV 100 rotary viscometer. Sinusoidally time varying simple shear is superimposed on a constant simple shear caused by rotation of a sensor in the liquid to be measured. The phase shift between (i) the sine wave signal applied to drive the sensor and (ii) the signal generated by a pickup responsive to the motion of the sensor in the liquid, is measured. The storage modulus is determined from the phase shift data by a suitable computer program.

Both the relaxation and dynamic types of Haake viscoelasticity determining rheometers are laboratory types which measure small samples and cannot be satisfactorily used for inline applications.

In the Bohlin VOR rheometer [sold by Bohlin, Inc., Science Park Ideon, University Site, Box 742, S-220 07 Lund, Sweden], a small amplitude oscillatory shearing motion is used to measure the ability of a liquid to store elastic energy and dissipate viscous energy. This offline rheometer requires that small samples be delivered to it for measurement. The Bohlin rheometer is a laboratory instrument and not a process control instrument.

The Seiscor/Han rheometer [sold by Seiscor Corp., P.O. Box 1590, Tulsa, Okla. 74102], provides continuous online viscoelasticity measurements at high shear rates. The polymeric or other viscoelastic liquid is caused to flow through a long slit, so that recoverable elastic energy is stored in the liquid because of the viscous resistance of the wall of the slit. For a constant velocity profile, the pressure gradient along the slit is related to the viscosity and the exit pressure is related to the elasticity. For a Newtonian liquid there is no exit pressure. This rheometer as it is presently constructed is not an inline instrument. It requires accurate slit design, two zones of temperature control and accurately placed pressure transducers with the aid of sophisticated microprocessing technology.

The viscoelasticity rheometer produced by Rheometrics, Inc. [1 Possumtown Road, Piscataway, N.J. 08854] operates in a side-stream. This instrument has a sensor comprising concentric cylinders, the outer cylinder shearing the liquid in an oscillatory manner, and the inner cylinder being driven by the sheared liquid. The amplitude and phase of the induced periodic torque on the inner cylinder are compared with the amplitude and phase of the oscillation of the outer cylinder respectively. From the difference signals the loss modulus and storage modulus of the liquid are determined. This is not an inline instrument. U.S. Pat. No. 4,468,953 of R. F. Garritano describes a rheometer of this type.

Online and laboratory instruments for the measurement of viscoelasticity of liquids also are described in Rheometers for Molten Plastics by John M. Dealy, published by Van Nostrand Rheinhold Co., 135 W. 50th Street, New York, N.Y. 10020 (1982); and in Viscoelastic Properties of Polymers, 3rd Ed., by John D. Ferry, published by John Wiley & Sons, Inc., New York, N.Y. (1980).

Accordingly, an object of the present invention is to provide a rheometer and a measurement method capable of reliable linear viscoelasticity measurements.

Another object of the invention is to provide such a rheometer in a form suitable for inline process control applications.

Another object of the invention is to provide such a rheometer in a form capable of rapid and continuous operation at elevated pressures and temperatures, without rotating parts in contact with the liquid, so that the rheometer can reliably detect viscoelasticity exhibited by slurries such as foods and minerals.

SUMMARY OF THE INVENTION

According to one aspect of the invention, there is provided apparatus for determining an elastic property of a viscoelastic liquid. The apparatus comprises a transducer comprising a transducer body and a transducer tip adapted to be immersed in a viscoelastic liquid, with means for driving the transducer so that the tip oscillates at a frequency determined by the mechanical characteristics of the transducer. Control circuitry drives the transducer to provide a constant amplitude of oscillation, regardless of the viscous load on the tip. Means is provided for determining the frequency of oscillation $f_A$ of the tip in a reference fluid, and for determining the frequency of oscillation $f_L$ of the tip in the viscoelastic liquid. Means is also provided for determining a parameter of the viscoelastic liquid as a function of the change in power required to drive the transducer in order to maintain a constant amplitude of oscillation of the tip thereof when the transducer tip is immersed in the liquid and ($f_A - f_L$). Means is also provided for determining a parameter of the viscoelastic liquid which is a measure of the elasticity thereof, as a function of the input power and $f_A - f_L$.

According to another aspect of the invention, there is provided a method for determining an elastic property of a viscoelastic liquid. The method comprises the steps of providing a transducer comprising a transducer body and a transducer tip adapted to be immersed in a viscoelastic liquid. The transducer is driven so that the transducer tip oscillates at a frequency determined by the mechanical characteristics of the transducer with a constant amplitude, regardless of the load on the tip. The transducer tip is disposed in a reference fluid such as air, and the corresponding frequency of oscillation $f_A$ of the transducer tip is determined. The transducer tip is immersed in the viscoelastic liquid, and the corresponding frequency of oscillation $f_L$ of the tip is determined. The viscous loss of the viscoelastic liquid is determined as a function of the increase in power required to drive the transducer in order to maintain a constant amplitude of oscillation of the tip thereof when the tip is immersed in said liquid and $f_A - f_L$. A parameter of the viscoelastic liquid which is a measure of the elasticity thereof is determined as a function of the input power and $f_A - f_L$.

IN THE DRAWING

SYSTEM OVERVIEW

Figure 1:
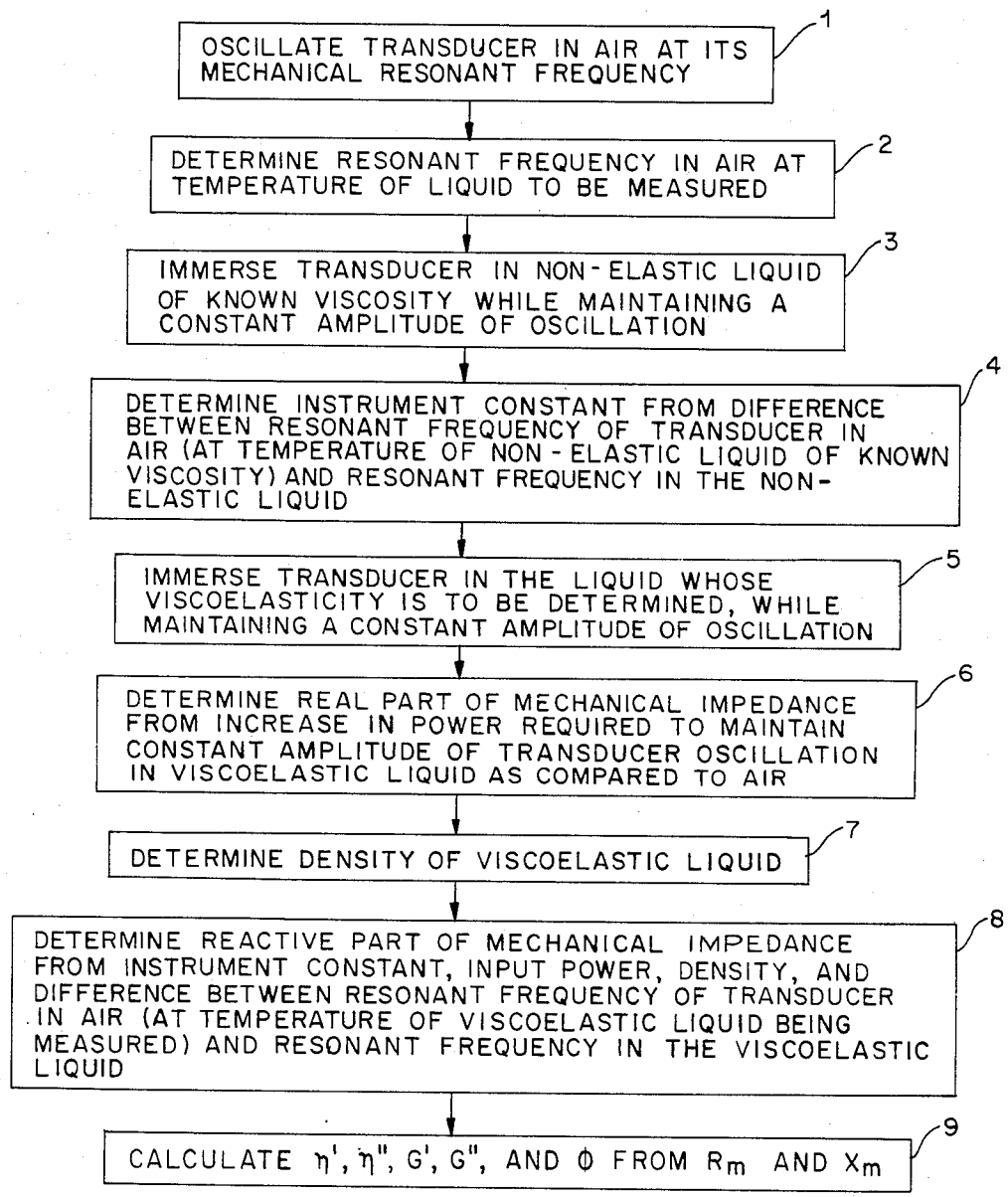
FIG. 1 is a diagram showing the functional steps involved in determining viscoelasticity according to a preferred embodiment of the invention.

As detailed in the Theoretical Basis portion of this specification which follows, mathematical relationships have been developed that permit the determination of viscoelasticity of liquids from the "nominal viscosity" and frequency shift to which a transducer oscillating at its mechanical resonant frequency is subjected when the transducer is immersed in the liquid and maintained at a constant amplitude of mechanical oscillation.

Viscometers employing such transducers are known in the art. The transducer and associated circuitry shown, for example, in U.S. Pat. No. 4,488,427 entitled Rotational Vibratory Viscometer Transducer and Circuit may be employed as a portion of the rheometer of the present invention; it being preferred, however, that the immersible end of the transducer be a cylinder because its theoretical performance is more easily predicted. However, the sphere shown in the drawing of said patent can alternatively be employed with satisfactory results.

Alternatively, the transducer and associated circuitry shown in U.S. Pat. No. 4,524,610 entitled In-Line Vibratory Viscometer Densitometer may be employed.

A disposable transducer sensor tip which is detachably secured to the end of the compliant sheath of the transducer also can be used.

Each of these viscometers has a feedback control circuit which causes the transducer to torsionally oscillate at a constant amplitude of mechanical oscillation, at the mechanical resonant frequency of the transducer. The increase in power required to maintain the same amplitude when the transducer is immersed in a liquid is a measure of the real part of the mechanical impedance of the liquid. U.S. Pat. No. 4,524,610 also has the capability of determining the density of the liquid in connection with a flexural mode of oscillation of the transducer, on an inline basis.

Figure 3:
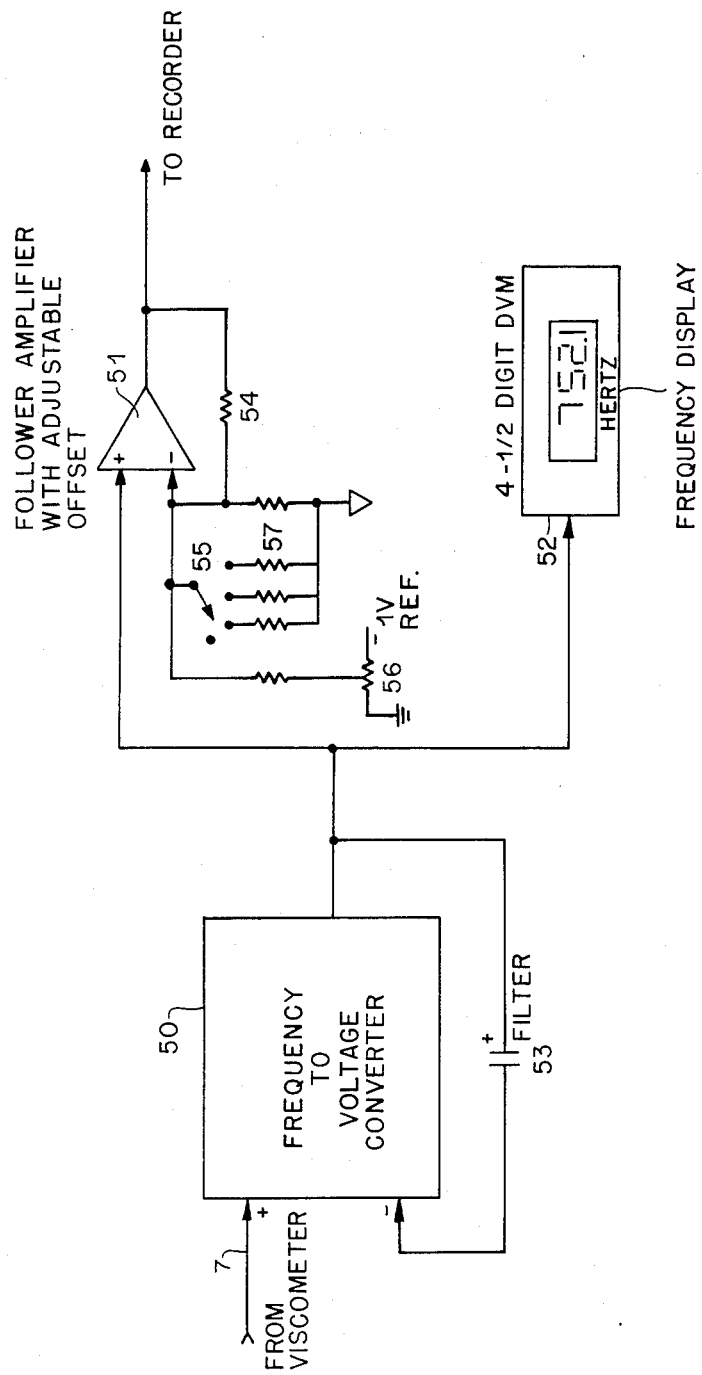
FIG. 3 is a block diagram of the frequency-to-voltage converter, frequency display and frequency recorder units shown in FIG. 2.
Figure 6:
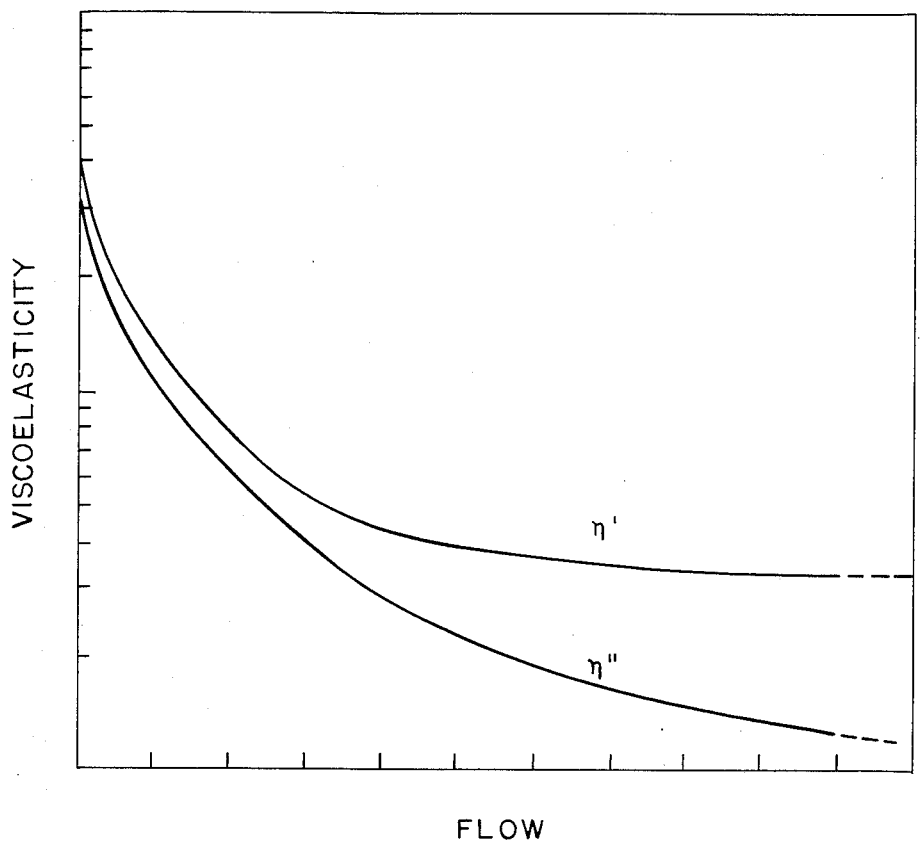
FIG. 6 is a chart showing the viscous loss and elasticity of a typical viscoelastic liquid (tomato paste) as a function of flow rate.

Each of these transducers has an AC signal available, the frequency of which signal is exactly equal to the frequency of mechanical torsional oscillation of the associated transducer. In U.S. Pat. No. 4,488,427 this signal appears at the output of the amplitude monitoring circuit 6 on line 7, as shown in FIG. 3 of the patent; while in U.S. Pat. No. 4,524,610 this signal appears at the output of the amplitude monitoring circuit 6 on line 7 within block 11, as shown in FIG. 6 of the patent.

By precisely converting the frequency of this AC signal to a DC signal and accurately measuring the DC signal (or by digitally counting the cycles of the AC signal), the exact frequency of mechanical torsional oscillation of the transducer may be determined [in either event it is desirable to integrate or filter the data so as to reduce noise and improve the frequency resolution]. Such an exact determination of frequency is essential in the present invention, since the frequency shifts which occur when the transducer is immersed in many liquids are a small percentage of the resonant frequency of oscillation of the transducer in air; and very accurate frequency shift data is required for the accurate determination of viscoelasticity according to the present invention.

Once the real part of the mechanical impedance and frequency are determined, the viscoelasticity is determined according to the mathematical relationships which have been developed.

The method employed in determining viscoelasticity according to a preferred embodiment of the present invention is outlined in FIG. 1, and consists of eight steps. Of these, Steps 1 to 4 are instrument calibration steps which need to be done only occasionally, so that measurement steps 5 through 8 can be carried out on a continuous inline basis suitable for process control applications.

The method outlined in FIG. 1 and carried out by the apparatus of FIGS. 2 to 5 is capable of measuring the viscoelasticity of flowing liquids and is specially applicable to continuous process control of viscoelasticity and also is useful as a laboratory instrument. Manual laboratory measurements typically take less than one-half minute to complete, the time involved being essentially the time it takes to immerse and clean the immersible transducer tip. The manual laboratory measurements of viscoelasticity provided by the arrangement of the present invention are accurate over a broad range of viscoelasticity.

Referring to FIG. 1, at Step 1 the transducer is caused to (preferably torsionally) oscillate in air at its mechanical resonant frequency, in the manner provided for by the aforementioned patents, and the frequency of oscillation is determined and stored.

At Step 2 the determined frequency of oscillation is corrected for the temperature difference between the air and the non-elastic liquid in which the transducer tip is to be immersed for calibration purposes. It has been found that the frequency of oscillation of the transducer in air varies linearly with temperature over a wide temperature range, thus providing for a relatively simple temperature correction. This corrected frequency value is stored.

At Step 3 the transducer tip is immersed in a non-elastic reference liquid of known viscosity, while the control circuitry of the rheometer maintains a constant amplitude of mechanical oscillation. As a result, there is a decrease in the resonant frequency of mechanical oscillation, and additional power must be supplied to the transducer drive circuit to maintain the same amplitude of oscillation as the transducer had in air.

At Step 4 an instrument constant is determined from the known characteristics of the reference liquid and the (corrected for temperature difference between the liquid and the air) frequency shift due to immersion of the transducer tip in the liquid, to complete the calibration process. The instrument constant is stored.

At Step 5 the transducer tip is immersed in the liquid the viscoelasticity of which is to be determined, while the control circuitry maintains a constant amplitude of mechanical oscillation of the transducer tip at its mechanical resonant frequency.

At Step 6 the real part of the mechanical impedance (viscosity-density product) is determined (according to the teachings of the aforementioned U.S. Pat. Nos. 4,488,427 and 4,524,610 for example) from the increase in power required to maintain a constant amplitude of transducer oscillation in the liquid being measured. This mechanical resistance value is stored.

At Step 7 the density of the liquid being measured is determined and stored. The density of the liquid may be determined by a separate densitometer or by the densitometer incorporated in the device described in U.S. Pat. No. 4,524,610.

At Step 8 a computer program hereafter described corrects the frequency of oscillation of the transducer in air for the temperature difference between air and the liquid being measured, and utilizes the data previously stored to determine (i) the elastic component of viscosity and/or (ii) the storage modulus of the liquid being measured, and also performs corrections taking into account the cylindrical or spherical geometry of the sensor.

At Step 9 the values of $\eta'$, $\eta''$, $G'$, $G''$ and $\phi$ are computed from $R_m$ and $X_m$.

THEORETICAL BASIS OF THE INVENTION

Figure 2:
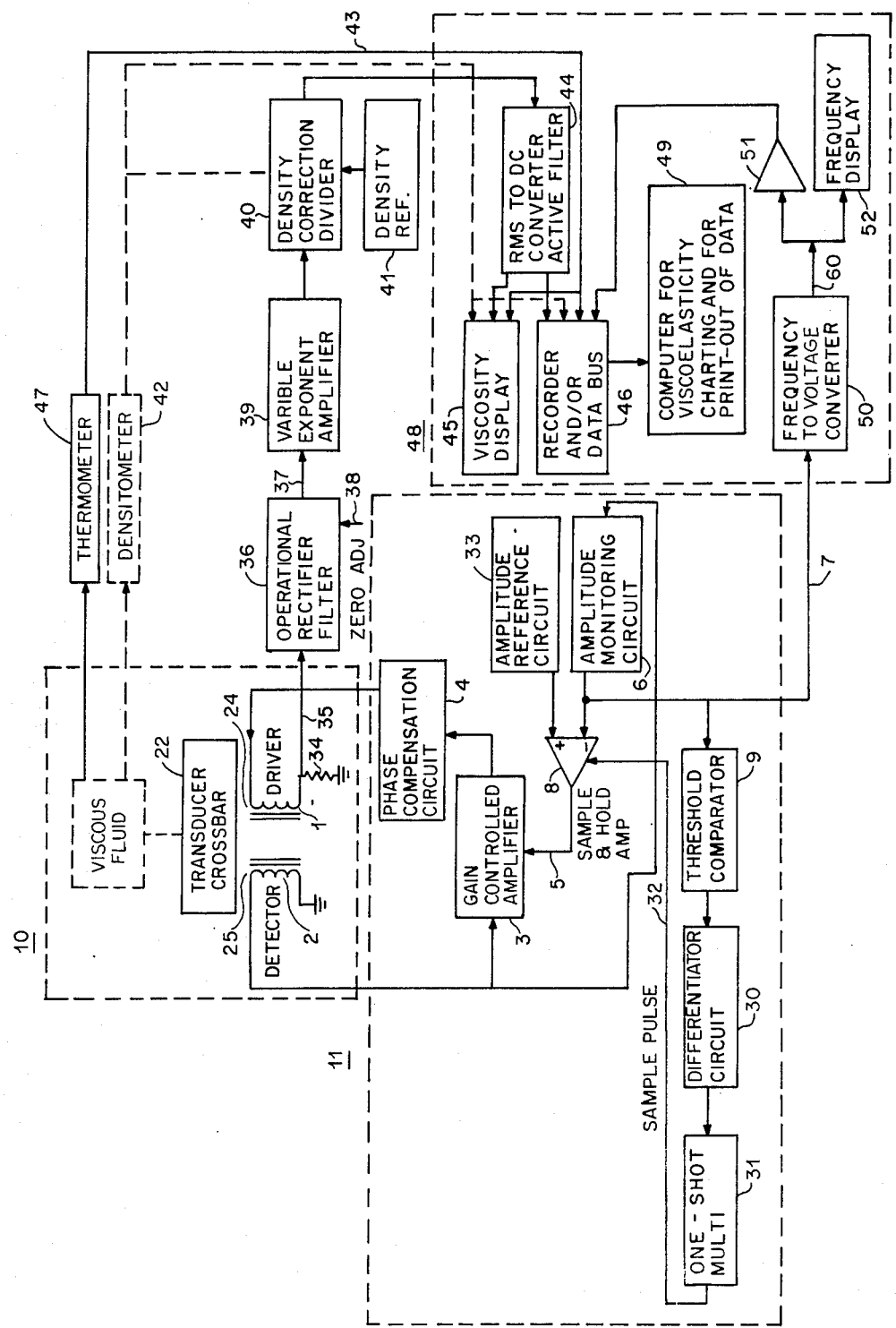
FIG. 2 is a functional block diagram of a viscoelasticity rheometer according to a preferred embodiment of the present invention.

According to the invention, viscoelasticity is computed by the rheometer shown in FIG. 2 from measurements of the real part of the mechanical impedance/resonance frequency shift of the transducer tip upon immersion in a viscoelastic liquid. Power is automatically provided in order to maintain a constant amplitude of mechanical oscillation. The rheometer squares the current supplied to the electromagnetic coil which drives the transducer to yield a signal corresponding to the drive power required, said signal being proportional to the corresponding real part of the mechanical impedance experienced by the oscillating surface of the transducer tip.

The rheometer is calibrated utilizing two calibration processes, namely:

(i) to correlate instrument readings of viscosity or viscosity-density product with the corresponding values of reference viscous liquids according to the teachings of the aforementioned patents; and (ii) to determine the instrument constant for calculation of one or more viscoelasticity parameters, so that viscoelasticity readings can be reliably reproduced from one instrument to another.

According to the second calibration process, the rheometer is calibrated by means of standard non-elastic viscous liquids, since the mathematics set forth below facilitates such calibration, and because no recognized standard viscoelastic liquids are presently available. However, if a standard viscoelastic liquid were to become available, the same could be used for checking the precision of the rheometer.

A non-elastic viscous liquid produces a significant shift in resonance frequency between the air value and the liquid value. A very elastic liquid produces only a small frequency shift.

A viscoelastic liquid is usually mathematically conceptualized by considering it to have a complex viscosity $\eta^*$ consisting of a real viscous loss component and an imaginary elastic component. Thus visco-elasticity is usually expressed in terms of the complex modulus $G^*$ or complex viscosity $\eta^*$ as follows:

$$\eta^* = \eta' - i\eta'' = \eta_m e^{-i\phi} \quad (1)$$

and $$\eta_m = \sqrt{\eta'^2 + \eta''^2} \quad (2)$$

and $$G^* = G' + iG'' = i\omega\eta^* \quad (3)$$

Where:

$\eta'$ is the true viscosity or viscous loss component.
$\eta''$ is the elastic component.
$\eta_m$ is the absolute value of the complex viscosity
$G'$ is the storage modulus
$G''$ is the loss modulus $\omega$ is the transducer resonant oscillation frequency in radians/second [corresponding to $2\pi f$, where f is the transducer resonant oscillation frequency in Hertz]

$\phi$ angle of complex viscosity

The mathematics described below assumes that the surface of the transducer tip is planar and oscillates in the direction of the plane thereof at a constant amplitude. In a typical rheometer according to the present invention, the amplitude of circumferential movement of the surface of the transducer tip is on the order of 1 micron, while the radius thereof is on the order of 1.5 cm. $= 1.5 \times 10^4$ microns. The ratio of radius to oscillation amplitude is so great that the surface may be equated to a plane without significant error. Alternatively, the transducer tip can be a plate which oscillates in a direction of its plane.

The (complex) mechanical impedance $Z^*$ presented by the liquid to the oscillating surface of the (preferably but not necessarily cylindrical) transducer tip is given by $$Z^* = R_m + iX_m \quad (4)$$

Where $R_m$ is the mechanical resistance presented by the liquid to the oscillating surface of the transducer tip $X_m$ is the mechanical reactance presented by the liquid to the oscillating surface of the transducer tip and $$Z^* = \sqrt{i\omega\rho\eta^*} \quad (5)$$

Where $\rho$ is the density of the viscoelastic liquid

By combining equations (4) and (5) above:

$$Z^2 = [i(\eta_m' - i\eta_m'')\omega\rho] = (R_m - iX_m)^2$$

$$R_m^2 + 2iR_mX_m - X_m^2 = i\omega\rho(\eta' - i\eta'') = \omega\rho(i\eta' + \eta'')$$

$$\eta_m' = \frac{2R_mX_m}{\omega\rho} \quad (6)$$

$$\eta_m'' = \frac{R_m^2 - X_m^2}{\omega\rho} \quad (7)$$

Referring to equations (4) and (5), $$Z^* = R_m + iX_m = \sqrt{G^*\rho} = \sqrt{i\omega\rho\eta^*}$$

$$= \left(e^{i\frac{\pi}{2}} \eta_m e^{-i\phi} \omega\rho\right)^{\frac{1}{2}}$$

Where $\phi$ is the angle of the complex viscosity coefficient, i.e. $\phi = \arctan \eta''/\eta'$ $$R_m + iX_m = \left\{\eta_m\omega\rho e^{[i(\frac{\pi}{2} - \phi)]}\right\}^{\frac{1}{2}}$$

$$R_m + iX_m = \sqrt{\eta_m\omega\rho} \left\{e^{[i(\frac{\pi}{2} - \phi)]}\right\}^{\frac{1}{2}}$$

$$R_m + iX_m = \sqrt{\omega\eta_m\rho} \left[\cos\left(\frac{\pi}{4} - \frac{\phi}{2}\right) + i\sin\left(\frac{\pi}{4} - \frac{\phi}{2}\right)\right]$$

Therefore $$R_m = \sqrt{\omega\eta_m\rho} \cos\left(\frac{\pi}{4} - \frac{\phi}{2}\right) \quad (8)$$

and $$X_m = \sqrt{\omega\eta_m\rho} \sin\left(\frac{\pi}{4} - \frac{\phi}{2}\right) \quad (9)$$

and $R_m$ and $X_m$ can be determined as follows:

As mentioned above, the rheometer is calibrated in terms of the viscosity-density products of standard non-elastic viscous liquids. In this case the viscosity-density product is proportional to the average power P required to overcome the mechanical resistance of the liquid and maintain a constant amplitude of oscillation of the transducer tip. Thus the viscosity-density product is proportional to the mechanical resistance component $R_m$ of the complex impedance $Z^*$.

The rheometer displays the quantity $\eta_n\rho$ which is the "nominal viscosity-density" product, where $\eta_n$ is defined by the following equation:

$$\eta_n = k\overline{P} = kR_m \quad (10)$$

Where k is a parameter which is a function of the resonant frequency and the amplitude of oscillation of the transducer tip surface, and is a constant for a particular instrument.

Since $$\eta^* = \eta' - i\eta'' = \eta_m e^{-i\phi} = \eta_m(\cos\phi - i\sin\phi)$$

$$\eta' = \eta_m \cos\phi \quad (11)$$

$$\eta'' = \eta_m \sin\phi \quad (12)$$

and by squaring Equation (8)

$$R_m^2 = \omega\eta_m\rho \cos^2\left(\frac{\pi}{4} - \frac{\phi}{2}\right)$$

$$= \omega\eta_m\rho \left\{\frac{1}{2}\left[1 + \cos\left(\frac{\pi}{2} - \phi\right)\right]\right\}$$

$$= \frac{\omega\eta_m\rho}{2} \left[1 + \cos\frac{\pi}{2}\cos\phi + \sin\frac{\pi}{2}\sin\phi\right]$$

$$= \frac{\omega\eta_m\rho}{2}(1 + \sin\phi) = \frac{\omega\eta_m\rho}{2} + \frac{\omega\eta_m\rho}{2}\sin\phi$$

Equation 10 shows that $\eta_n$ is proportional to $R_m$. Combining Equations 10 and 12, $$R_m^2 = \frac{\omega\rho}{2}(\eta_m + \eta'') = \frac{\omega}{2}\eta_n\rho$$

From the above equation the viscosity-density readout of the rheometer is given by $$\eta_n\rho = \eta_m\rho + \eta''\rho$$

Therefore $$\eta_n = \eta_m + \eta''$$

and $$R_m = \sqrt{\pi f_L \eta_n \rho} \quad (14)$$

This value of $R_m$ is used in Equations (6) and (7) to determine the real and imaginary components of the complex viscosity.

In the case of a cylindrical transducer tip the mechanical reactance is predicted by the following equation:

$$X_m = \left(\frac{I}{\pi a^3(2l + a)}\right)\left(\frac{\omega_A^2 - \omega_L^2}{\omega_L}\right) \quad (15)$$

Where
I is the moment of inertia of the transducer about an axis of oscillation coinciding with the longitudinal axis of the cylinder
a is the radius of the cylinder
l is the length of the cylinder
$\omega_A$ is the mechanical resonant frequency of the transducer in air, in radians per second
$\omega_L$ is the mechanical resonant frequency of the transducer in the liquid, in radians per second This theoretical prediction of mechanical reactance is not a totally accurate predictor of actual results, however, due to deviation of the actual apparatus and its operation from the theoretical ideal. Therefore it is necessary to determine the mechanical reactance empirically by use of the method and apparatus of the present invention.

Each instrument has a characteristic defined by the instrument constant K:

$$K = X_m\left(\frac{\omega_L}{\omega_A^2 - \omega_L^2}\right) \quad (16)$$

Standard non-elastic viscous liquids (which have the property that the mechanical resistance is equal to the mechanical reactance thereof) are used to determine the instrument constant K according to the following equations:

$$K = \frac{(R_m = X_m)f_{LT}}{2\pi(f_{AT}^2 - f_{LT}^2)} = \frac{\sqrt{\pi f_{LT}\rho\eta_m}}{4\pi(f_{AT} - f_{LT})} \quad (17)$$

Where
$f_{AT}$ is the transducer mechanical oscillation frequency in air at the temperature of the liquid to be measured
$f_{LT}$ is the transducer mechanical oscillation frequency in the liquid to be measured For the purpose of determining the complex viscosity of viscoelastic liquids by means of Equations 6 and 7, the mechanical reactance is obtained by restating Equation 17 as follows:

$$X_m = K 2\pi\left(\frac{f_{AT}^2 - f_{LT}^2}{f_{LT}}\right) \quad (18)$$

The rheometer transducers that were tested were found to have resonant frequencies which varied linearly with temperature over a wide range. For such transducers the frequency of mechanical oscillation in air at the temperature at which the liquid measurement is to be conducted is given by $$f_{AT} = f_A - c(T - 20) \quad (19)$$

Where
$f_A$ is the resonant frequency of mechanical oscillation in air at 20 degrees Centigrade
c is the temperature coefficient of frequency variation of the transducer
T is the temperature at which the liquid measurement is to be conducted.

DETAILED DESCRIPTION

Figure 4:
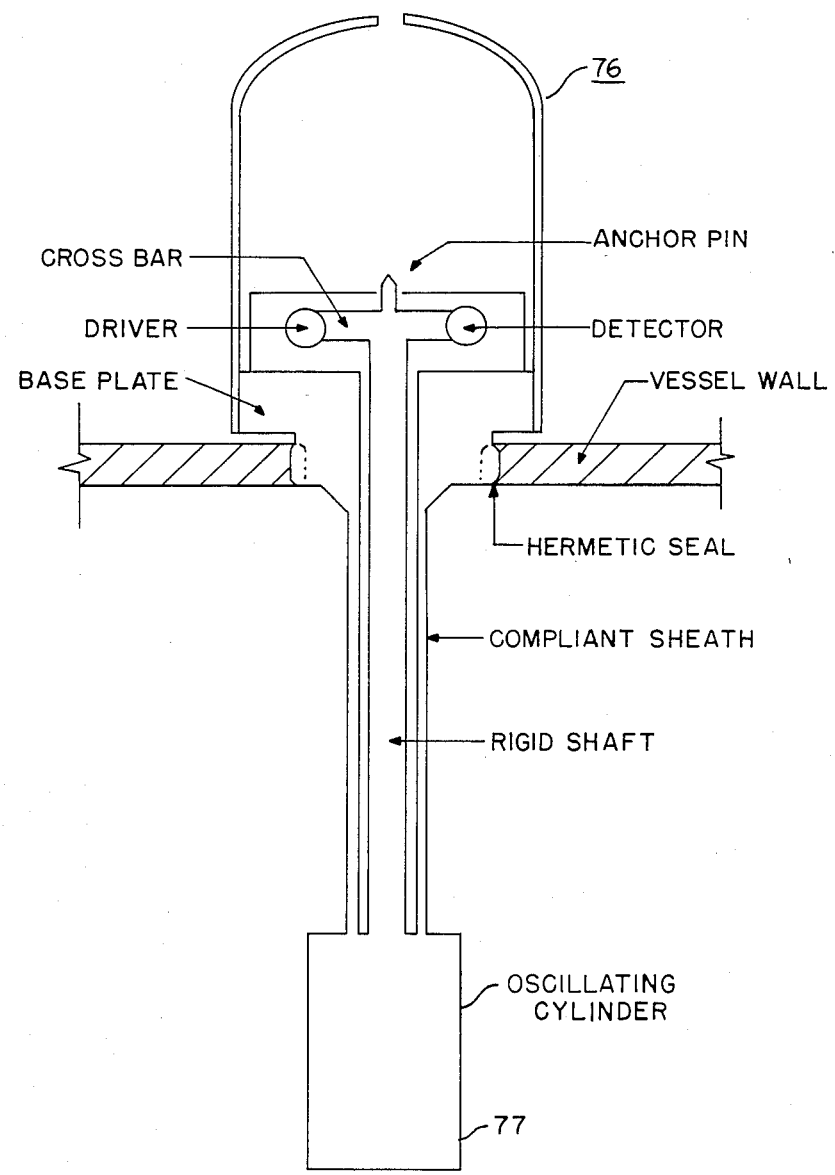
FIG. 4 is a cross-sectional schematic view of a preferred form of the transducer employed in the rheometer shown in FIG. 2.

In the block diagram of FIG. 2, blocks 1 through 46 are identical to the corresponding blocks shown in FIG. 3 of U.S. Pat. No. 4,488,427, the disclosure of which is incorporated herein by reference. The transducer shown in FIGS. 1 and 2 of said patent is identical to the transducer shown in FIG. 4 of the present application, except that the transducer tip shown in FIG. 4 is in the form of an enclosed cylinder. However, although a cylindrical tip is preferred, for ease of cleaning a spherical transducer tip as shown in U.S. Pat. No. 4,488,427, or some other form of tip, can be utilized.

As shown in block 10 of FIG. 2, the transducer crossbar 22 is caused to oscillate at constant amplitude by the feedback control circuit shown in block 11; and the transducer tip which is immersed in air (for calibration purposes) or a liquid and is mechanically connected to the crossbar is caused to oscillate in torsion accordingly at the mechanical resonant frequency of the transducer.

The arrangement shown in block 48 of FIG. 2 determines the viscoelasticity (i.e. the elastic and viscous components of the complex viscosity coefficient from the input power signal on line 43 [which indicates the so-called "nominal viscosity" when the density correction divider 40 is utilized, and which indicates the "nominal viscosity-density" product when the density correction divider is bypassed], a liquid density signal (obtained from the densitometer 42, a densitometer independent of the rheometer, or information obtained from tables or the like. Displays of oscillation frequency and the elastic or storage component of viscous loss or true viscosity as a function of time, as well as liquid temperature and density are also provided.

The AC signal output of amplitude monitoring circuit 6 on line 7 (at a frequency equal to the mechanical oscillation frequency of the transducer) is coupled to a very stable frequency-to-voltage converter 50 which converts the frequency of the AC signal to a corresponding voltage for display and computation purposes. Alternatively, a digital counting circuit could be used to convert the AC signal on line 7 to a frequency-indicating digital signal.

The output of converter 50 on line 60 is coupled to voltage follower 51, the function of which is to expand the small voltage variation to the signal on line 60 (corresponding to the small frequency shifts produced by most viscoelastic liquids) to provide an increased dynamic range of the frequency indicating signal, and thus to improve the resolution of the rheometer. The output of converter 50 is also coupled to a digital voltmeter 52, which provides a digital display of oscillation frequency. The output of voltage follower 51 is coupled to computer 49 via data bus 46.

Blocks 50, 51 and 52 are shown in greater detail in FIG. 3.

The device preferred for the frequency-to-voltage converter 50 Model 451K made by Analog Devices, Inc. of Massachusetts. This device has a differential input, and it was found that use of a 10 microfarad integrating filter capacitor 53 reduced noise and thus improved the frequency resolution of the rheometer.

The dynamic-range-expanding voltage follower amplifier 51 has adjustable gain and offset. The gain of the amplifier is set by a combination of the feedback resistor 54 and the parallel combination of input resistors 57. Various gains are selectable by switch 56; with the lowest gain giving the maximum frequency range, the smallest dynamic range, and the greatest stability. Higher gain gives greater dynamic range and improved frequency resolution but less stability.

At high gain settings an offset voltage is necessary to bring the output voltage within the scale limits of the recorder/data bus 46. The offset is provided by a potentiometer circuit 56 connected to a highly stable reference source.

If it is desired to reduce the cost of the rheometer, the recorder can be dispensed with, and the output of the follower amplifier 51 can also be coupled (through a selection switch) to the voltmeter 52, so that a 6 digit frequency readout is effectively displayed on the 4½ digit voltmeter 52, the two most significant digits being omitted by the adjustable gain and offset circuits of the voltage follower 51. Calibration of the third most significant digit is provided by a 10-turn potentiometer 56 equipped with a counting dial for resetting. With this arrangement the readout of DC voltmeter 52 represents a zero to 10 Hertz frequency shift range, with three significant figures after the decimal.

For example, a transducer mechanical oscillation frequency of 752.321 Hz will be seen and shown by the voltmeter 52 as 2.321±0.001 Hz. [The setting error between the primary display of 752.3 Hz±0.1 Hz and the expanded secondary display of 2.321 Hz. can cause meshing offset of ±1.000 Hz which is easily detected in the measurements and then corrected for.]. The three figures after the decimal in the expanded display enable small frequency changes to be accurately determined.

Where cost reduction is not such an important factor, substantially more expensive digital D.C. voltmeters with 6½ digit resolution may be provided, to directly display small frequency changes to three significant figures after the decimal.

Figure 5:
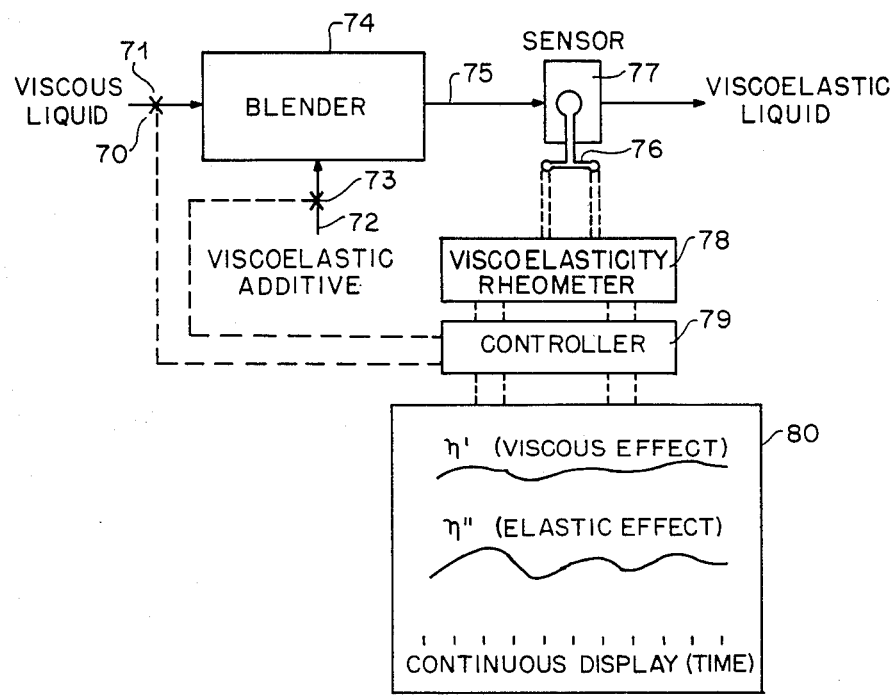
FIG. 5 is a block diagram of an inline process control system utilizing the rheometer shown in FIG. 2.

With the computer 49 implementing the equations set forth in the preceding theoretical analysis portion of this specification, the complex viscosity and viscoelasticity parameters of the viscoelastic liquid and the frequency of oscillation may be displayed, recorded, converted and charted as shown in FIG. 5. FIG. 6 illustrates typical variations in the real and imaginary components of viscosity of a viscoelastic fluid, as obtained with the method and apparatus of the present invention.

Computer Program for Determining Viscoelasticity Parameters

A simple program may be used for computing the viscoelasticity parameters from the frequency shift of the transducer and the measured "nominal viscosity" of the liquid. This program is based on the equations derived in the preceding Theoretical Basis section of this specification and was successfully run on a McIntosh computer, manufactured by Apple Computer Company, Inc., Mariana Ave., Cupertino, Calif. 95014. The program was developed utilizing a TK! Solver program sold by Software Arts, 27 Mica Lane, Wellesly, Mass. 02181; and employs "Rules" written in the format required by the program.

The correlation between the symbols employed in the program and the symbols used in the Theoretical Basis portion of this specification is as follows:

| Theoretical Basis Portion of Specification | Description | Unit | Program |
|---|---|---|---|
| $\left(\dfrac{\pi}{4} - \dfrac{\phi}{2}\right)$ | Difference between 45 degrees and half of the complex viscosity angle | Radians | i |
| c | Temperature coefficient of frequency variation of transducer | | c |
| $f_A$ | Frequency of oscillation in air at 20 degrees C. | Hertz | FF |
| $f_{AT}$ | Frequency of oscillation in air at temperature T | Hertz | F |
| $f_{LT}$ | Frequency of oscillation in liquid at temperature T | Hertz | f |
| $f_{AT} - f_{LT}$ | Frequency shift due to liquid | Hertz | b |
| G' | Storage modulus of liquid | (dynes/cm$^2$) | G |
| G'' | Loss modulus of liquid | (dynes/cm$^2$) | GG |
| K | Instrument constant | g/cm$^2$ | K |
| r | Ratio of elastic term to viscous term of $\eta^*$, i.e. $\eta''/\eta'$ | none | r |
| $R_m$ | Mechanical resistance presented to transducer tip by liquid, as computed by Equation 8 | g/cm · sec. | R1 |
| $R_m$ | Mechanical resistance presented to transducer tip by liquid, as computed by Equation 14 | g/cm · sec. | R |
| $T_L$ | Temperature of measurement | Degrees C. | T |
| $X_m$ | Mechanical reactance presented to transducer tip by liquid, as computed by Equation 9 | g/cm · sec. | X1 |
| $X_m$ | Mechanical reactance presented to transducer tip by liquid, as computed by Equation 18 | g/cm · sec. | X |
| $\phi$ | Angle of complex viscosity | Radians | z |

-continued

| Theoretical Basis Portion of Specification | Description | Unit | Program |
|---|---|---|---|
| $\eta_n$ | "Nominal viscosity" by rheometer readout | Poise | N |
| $\eta'$ | Viscous loss component by complex viscosity coefficient | Poise | nd |
| $\eta''$ | Elastic component of complex viscosity coefficient | Poise | NN |
| $\eta_m$ | Absolute value of complex viscosity coefficient | Poise | b |
| $\rho$ | Density of liquid | g/cm³ | d |

The "Rules" employed by the program for a transducer having a frequency-temperature coefficient of 0.700±0.0005 Hz./deg. C. (from below 20 deg. C. to 200 deg. C.) are as follows [the number of the corresponding equation(s) which appears in the Theoretical Basis portion of this specification is set forth to the right of each rule]:

| | | |
|---|---|---|
| 1. | F = FF − (c)*(T − 20) | (19) |
| 2. | R = SQRT(PI()*f*n*d) | (14) |
| 3. | X = K*2*PI()*((F 2−f 2)/f) | (18) |
| 4. | N = (R*X)/(PI()*f*d) | (16) |
| 5. | NN = (R 2−X 2)/(2*PI()*f*d) | (7) |
| 6. | nn = SQRT(N 2 + NN 2) | (2) |
| 7. | G = NN*2*PI()*f | (3) |
| 8. | GG = N*2*PI()*f | (3) |
| 9. | r = NN/N | |
| 10. | R1 = (SQRT(2*PI()*f*d*nn))*cos(.785 − z/2) | (8) |
| 11. | X1 = (SQRT(2*PI()*f*d*nn))*sin(.785 − z/2) | (9) |

From equation (17) which appears in the Theoretical Basis portion of this specification, the instrument constant is determined. The following printout is typical.

| Input | Symbol | Output | Comment |
|---|---|---|---|
| | | | K 5000 Standard |
| | q | 402.71692 | RULES: |
| | p | 149.6508 | K = q/p |
| | K | 2.6910442 | q = SQRT(PI()*f*n) |
| 639.7 | f | | p = 2*PI()*((F 2 − f 2)/f) |
| 80.7 | n | | |
| 651.5 | F | | |

Viscoelasticity determination by the program is illustrated by the following printout for a skin emollient:

| Input | Symbol | Output |
|---|---|---|
| .07 | c | |
| 1 | d | |
| 649.8 | f | |
| 9.49 | n | |
| | nn | 5.8069471 |
| | r | .82036741 |
| | z | .6870373 |
| | F | 651.745 |
| 651.99 | FF | |
| | G | 15037.219 |
| | GG | 18329.859 |
| 2.69 | K | |
| | N | 4.4895163 |
| | NN | 3.6830529 |
| | R | 139.18675 |
| | R1 | 139.21296 |
| 23.5 | T | |
| | X | 65.846279 |
| | X1 | 65.790854 | r is the ratio $\eta''/\eta'$ which is commonly used as an indicator of the degree of elasticity of a liquid. For the above skin emollient, r=0.820. For the relatively non-elastic standard S-600 referred to below, r=0.000223.

No recognized standard viscoelastic liquids suitable for checking the performance of the rheometer of the present invention are available. A rheometer with an instrument constant K of 3.73 g/cm² was used to measure a standard (non-elastic) viscous liquid S-600, with the following results:

| Input | Symbol | Output |
|---|---|---|
| 1 | d | |
| 724.01 | f | |
| 13.2 | n | |
| | nn | 13.197053 |
| | z | .00022333 |
| | F | 727.6965 |
| 727.7 | FF | |
| | G | 13.407274 |
| | GG | 60034.566 |
| 3.73 | K | |
| | N | 13.197052 |
| | NN | .00294724 |
| | R | 173.27431 |
| | R1 | 173.34327 |
| 20.05 | T | |
| | X | 173.23566 |
| | X1 | 173.16661 |

Process Control Applications

For process control applications the transducer is installed in a tank or pipeline so that its oscillatory tip is immersed in the liquid being processed. This enables the viscoelastic properties of the liquid to be automatically and/or manually monitored so as to enable control of the process to maintain a sufficient flow rate to produce a uniform product. The rheometer may be calibrated by a purely viscous (non-elastic) liquid before or after installation.

For example, FIG. 6 charts viscoelasticity of tomato paste as a function of flow rate. As the flow rate increases, the viscous loss falls to a steady value. The elasticity component of the complex viscosity coefficient falls more precipitously than does the viscous loss component, indicating how effectively the increased flow rate broke up the structure of the tomato paste.

The rheometer of the present invention is well suited for automatic process control. FIG. 5 is a diagram of a feedback control system for this purpose.

In the arrangement of FIG. 5, a viscous (non-elastic) liquid supplied via pipe 70 and valve 71 is blended in a blender 74 with a concentrated viscoelastic additive supplied via pipe 72 and valve 73, in order to produce a viscoelastic fluid which leaves the blender via pipe 75. The oscillatory sensor tip 77 of the transducer 76 (see FIG. 4) is disposed in the fluid path via a section of pipe coupled in the path of the pipe 75. The transducer is part of the rheometer 78 shown in FIG. 2.

The loss modulus G' and storage modulus G" outputs of the rheometer 78 are coupled to a process controller 79 and a real time display 80. The controller 79 compares these values with preset desired ranges thereof, and controls the valves 71 and 72 to vary the rates of flow of the liquids so as to maintain the values of G' and G" within the desired ranges.

The arrangement of FIG. 5 has many important process control applications. One such application is in the control of oil viscosity characteristics. At the present time only the low shear rate viscosity of blended multigrade motor oils is controlled; and this is done by the cumbersome and timeconsuming method of capillary off line measurement. One consequence is that the desired viscoelasticity must be guessed at. The rheometer of the present invention provides continuous viscoelastic information and composition adjustment on an inline basis, permitting current control of the process before the oil goes off specification, rather than guessing and after-the-fact corrective action as is now required.

If desired, the rate of flow of the viscous liquid in pipe 70 can be preset, with the valve 73 controlling the rate of introduction of the viscoelastic additive being responsive to the rheometer outputs. The desired elasticity level is achieved by controlling the flow rate of the additive into the blender.

For low viscosity liquids, viscoelastic measurements are achieved with greater precision by increasing the radius of the sensor tip and by weakening the spring constant of the compliant sheath of the transducer to increase its compliance (and reduce the frequency of oscillation). The frequency shift between air and the liquid will then be increased.

Viscoelastic measurements can be made at high pressures with suitable transducers like the one illustrated in FIG. 4. By changing the moment of inertia and/or the spring constant of the shaft and/or sheath of the transducer, the resonant frequency can be set over a wide range. Moreover, other resonant modes than the primary mode can be used; such as a mode 180 degrees out of phase with the primary mode which occurs when a spherical transducer tip is used.

Further, the second harmonic or a higher harmonic of the resonant frequency can be used, for enhanced resolution (although the signal may vary considerably in amplitude from the fundamental frequency signal). This can be done by utilizing a suitable filter to isolate the desired harmonic from the AC signal on line 7 of the output of the amplitude monitoring circuit of the rheometer (FIG. 2).

While the amplitude of oscillation must be constant for a given measurement, it can be varied between measurements.

I claim:

1. A method for determining an elastic property of a viscoelastic liquid, comprising the steps of:
   providing a transducer comprising a transducer body and a transducer tip adapted to be immersed in a viscoelastic liquid;
   driving the transducer so that the tip oscillates with a constant amplitude at the mechanical resonant frequency of the transducer, regardless of the viscous load on the tip;
   disposing the transducer tip in air, and determining the corresponding frequency of oscillation $f_A$ of the tip;
   correcting the value of $f_A$ to a value $f_{AT}$ for any difference in temperature between the air and the temperature of any liquid in which the tip is to be immersed, in the event the air temperature is significantly different from the temperature of the liquid;
   providing a reference liquid of known rheometric properties to be used for calibration purposes;
   immersing the transducer tip in said reference liquid, and determining the corresponding frequency of oscillation of the tip;
   determining an instrument constant as a function of the difference between the frequency $f_{AT}$ of the transducer tip in air and the frequency of the tip in the reference liquid;
   immersing the transducer tip in said viscoelastic liquid;
   determining the real part of the mechanical impedance of said viscoelastic liquid as a function of the increase in power required to drive said transducer in order to maintain a constant amplitude of oscillation of the tip thereof, as compared to the amount of power required to maintain said amplitude in air;
   determining the density of said viscoelastic liquid; and
   determining a parameter of said viscoelastic liquid which is a measure of the elasticity thereof, as a function of said instrument constant, real part of the mechanical impedance of said viscoelastic liquid, density, and $f_{AT}-f_{LT}$, where $f_{LT}$ is the frequency of oscillation of the transducer tip in said viscoelastic liquid.

2. The method according to claim 1, wherein said tip has more than one mode of oscillation, and said frequency of oscillation is the frequency of oscillation in a selected one of said modes.

3. The method according to claim 1, wherein said tip has a fundamental frequency of oscillation and one or more harmonic frequencies of oscillation, and said frequency of oscillation is the frequency of oscillation of the tip at a selected one of said harmonic frequencies.

4. A method for determining an elastic property of a viscoelastic liquid, comprising the steps of:
   providing a transducer comprising a transducer body and a transducer tip adapted to be immersed in a viscoelastic liquid;
   driving the transducer so that the tip oscillates at a frequency determined by the mechanical characteristics of the transducer with a constant amplitude, regardless of the viscous load on the tip;
   disposing the transducer tip in a reference fluid, and determining the corresponding frequency of oscillation $f_A$ of the tip;
   immersing the transducer tip in said viscoelastic liquid, and determining the corresponding frequency of oscillation $f_L$ of the tip;
   determining the real part of the mechanical impedance of said viscoelastic liquid as a function of the increase in power required to drive said transducer in order to maintain a constant amplitude of oscillation of the tip thereof when the tip is immersed in said liquid; and
   determining a parameter of said viscoelastic liquid which is a measure of the elasticity thereof, as a function of said real part of the mechanical impedance of said viscoelastic liquid and $f_A-f_L$.

5. The method according to claim 1 or 4, comprising the additional steps of:

subjecting said viscoelastic liquid to a predetermined process; and controlling said process in response to said parameter, so as to maintain the value of said parameter within a desired range.

6. A method for determining an elastic property of a viscoelastic liquid, comprising the steps of:

providing a transducer comprising a transducer body and a transducer tip adapted to be immersed in a viscoelastic liquid;

driving the transducer so that the tip oscillates at a frequency determined by the mechanical characteristics of the transducer with a constant amplitude, regardless of the viscous load on the tip;

disposing the transducer tip in a reference fluid, and determining the corresponding frequency of oscillation $f_A$ of the tip;

immersing the transducer tip in said viscoelastic liquid, and determining the corresponding frequency of oscillation $f_L$ of the tip;

determining the nominal viscosity of said viscoelastic liquid as a function of the increase in power required to drive said transducer in order to maintain a constant amplitude of oscillation of the tip thereof when the tip is immersed in said liquid; and determining parameter of said viscoelastic liquid which is a measure of the elasticity thereof, as a function of said nominal viscosity of said viscoelastic liquid and $f_A - f_L$.

7. Apparatus for determining an elastic property of a viscoelastic liquid utilizing a reference liquid of known rheological properties for calibration purposes, comprising:

a transducer comprising a transducer body and a transducer tip adapted to be immersed in a viscoelatic liquid;

means for driving the transducer so that the tip oscillates with a constant amplitude at the mechanical resonant frequency of the transducer, regardless of the mechanical load exerted by the liquid on the tip;

means for determining the frequency of oscillation $f_A$ of the tip in air;

means for correcting the value of $f_A$ to a value $f_{AT}$ for any difference in temperature between the air and the temperature of any liquid in which the tip is to be immersed, in the event the air temperature is significantly different from the temperature of the liquid;

means for determining the frequency of oscillation of the tip in a reference liquid;

means for determining an instrument constant as a function of the difference between the frequency $f_{AT}$ of the transducer tip in air and the frequency of the tip in the reference liquid;

means for determining the real part of the mechanical impedance of said viscoelastic liquid as a function of the increase in power required to drive said transducer in order to maintain a constant amplitude of oscillation of the tip thereof when said tip is immersed in said viscoelastic liquid, as compared to the amount of power required to maintain said amplitude in air; and means for determining a parameter of said viscoelastic liquid which is a measure of the elasticity thereof, as a function of said instrument constant, real part of the mechanical impedance of said viscoelastic liquid, density, and $f_{AT} - f_{LT}$, where $f_{LT}$ is the frequency of oscillation of the transducer tip in said viscoelastic liquid.

8. The apparatus according to claim 7, including:

means for providing an AC signal having a frequency equal to the frequency of oscillation of said transducer tip;

means for integrating said AC signal to reduce the noise content thereof;

means for converting said AC signal to a first DC signal proportional to the frequency thereof and having predetermined upper and lower limits; and dynamic range expansion means for converting said first DC signal to a second DC signal having upper and lower limits corresponding to a predetermined portion of the frequency range to which the upper and lower limits of said first DC signal correspond.

9. Apparatus for determining an elastic property of a viscoelastic liquid, comprising:

a transducer comprising a transducer body and a transducer tip adapted to be immersed in a viscoelastic liquid;

means for driving the transducer so that the tip oscillates at a frequency determined by the mechanical characteristics of the transducer with a constant amplitude, regardless of the mechanical load on the tip;

means for determining the frequency of oscillation $f_A$ of the tip in a reference fluid;

means for determining the frequency of oscillation $f_L$ of the tip in said viscoelastic liquid;

means for determining the real part of the mechanical impedance of said viscoelastic liquid as a function of the increase in power required to drive said transducer in order to maintain a constant amplitude of oscillation of the tip thereof when the tip is immersed in said liquid; and means for determining a parameter of said viscoelastic liquid which is a measure of the elasticity thereof, as a function of said real part of the mechanical impedance of said viscoelastic liquid and $f_A - f_L$.

10. The apparatus according to claim 7 or 8, further comprising:

process control means for processing said viscoelastic liquid; and means coupled to said parameter determining means for controlling said process control means so as to maintain the value of said parameter within a desired range.

* * * * *

UNITED STATES PATENT AND TRADEMARK OFFICE
CERTIFICATE OF CORRECTION

PATENT NO. : 4,754,640

DATED : July 5, 1988

INVENTOR(S) : J. Vincent Fitzgerald, Frank J. Matusik, Donald W. Nelson and John L. Schrag It is certified that error appears in the above-identified patent and that said Letters Patent is hereby corrected as shown below:

Column 12, line 55: change "g/cm·sec." to "g/cm$^2$·sec.";

Column 12, line 59: change "g/cm·sec." to "g/cm$^2$·sec.";

Column 12, line 64: change "g/cm·sec." to "g/cm$^2$·sec.";

Column 12, line 68: change "g/cm·sec." to "g/cm$^2$·sec.".

Signed and Sealed this

Twenty-ninth Day of November, 1988

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,754,640

DATED : July 5, 1988

INVENTOR(S) : J. Vincent Fitzgerald, Frank J. Matusik, Donald W. Nelson and John L. Schrag It is certified that error appears in the above-identified patent and that said Letters Patent is hereby corrected as shown below:

Column 8, line 15: change "P" to "$P^2$";

Column 8, line 16: insert "squared" after "resistance";

Column 8, line 19: insert "square" after "the";

Column 8, line 25: change "$\eta_n = k\overline{P} = kR_m$" to "$\eta_n = k\overline{P}^2 = kR_m^2$";

Column 8, line 53: insert "the square" after "to".

Signed and Sealed this

Thirtieth Day of May, 1989

Attest:

DONALD J. QUIGG

Attesting Officer

Commissioner of Patents and Trademarks